US00PP10366P

United States Patent [19]

Utecht

[11] Patent Number: Plant 10,366

[45] Date of Patent: Apr. 28, 1998

[54] GERANIUM PLANT NAMED 'FISDEL'

[75] Inventor: Angelika Utecht, Montabaur, Germany

[73] Assignee: Florfis AG, Binningen, Switzerland

[21] Appl. No.: 754,366

[22] Filed: Nov. 22, 1996

[51] Int. Cl.[6] ..... A01H 5/00

[52] U.S. Cl. ..... Plt./87.12

[58] Field of Search ..... Plt./87.12

[56] References Cited

PUBLICATIONS

GTITM UPOVROM Citation DE PBR PEL 01000 for 'Fisdel', Dec. 18, 1995.

GTITM UPOVROM Citation CA PBR 96–791 for 'Fisdel', Jul. 29, 1996.

*Primary Examiner*—James R. Feyrer

*Attorney, Agent, or Firm*—Foley & Lardner

[57] ABSTRACT

A new and distinct cultivar of geranium plant named 'Fisdel', particularly characterized by the combined features of violet double flowers in compact, uniform shaped umbels, intense green foliage with distinct zonation, early to medium flower response, and medium, very well branched plant habit.

1 Drawing Sheet

The present invention comprises a new and distinct cultivar of geranium, botanically known as *Pelargonium peltatum*, and hereinafter referred to by the cultivar name 'Fisdel'.

'Fisdel' is a product of a planned breeding program which had the objective of creating improved geranium cultivars with violet flower color, intense green foliage, and comparatively early flower response.

'Fisdell' was originated from a hybridization made by the inventor Angelika Utecht in a controlled breeding program in Galdar, Gran Canaria, Spain, in 1991. The female parent was the light violet colored variety 'Fisam', disclosed in U.S. Plant Pat. No. 8,327, and having double flowers, zoned foliage, and medium long, branched plant habit. The male parent of 'Fisdel' was the commercial variety 'Flocato', having semi-double violet flowers, zoned foliage and comparatively long trailing plant habit .

'Fisdel' was selected as one flowering plant within the progeny of the stated cross by Angelika Utecht in 1992 in a controlled environment in Galdar, Gran Canaria, Spain. The first act of asexual reproduction of 'Fisdel' was accomplished when vegetative cuttings were taken from the initial selection in Autumn 1992 in a controlled environment in Galdar, Gran Canaria, Spain, by, or under the supervision of, Angelika Utecht.

Horticultural examination of plants grown from these cuttings, initiated in May 1993 in Hillscheid, Federal Republic of Germany and continuing thereafter, has demonstrated that the combination of characteristics as herein disclosed for 'Fisdel' are firmly fixed and are retained through successive generations of asexual reproduction.

'Fisdel' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Fisdel', which in combination distinguish this geranium as a new and distinct cultivar:

1. Intense dark violet flower color.
2. Medium sized, round flowers and double flower form.

3. Intense green foliage with distinct zonation.
4. Medium long and very well branched plant habit.
5. Early to medium flower response.

Of the many commercial cultivars known to the present inventor, the most similar in comparison to 'Fisdel' are the parent cultivars 'Fisam' and 'Flocato', and the commercial variety 'Amethyst'.

Reference is made to attached Chart A which compares certain characteristics of 'Fisdel' to those same characteristics of 'Fisam' and 'Amethyst'. In general, comparison to 'Fisam', 'Fisdel' has a darker, more intense flower color, a more closed flower form, and markings on its upper petals. Plants of 'Fisam' and 'Fisdel' grow to about the same length, but plants of 'Fisdel' are better branched. The foliage of 'Fisdel' is somewhat more intense green and its leaves are smaller than those of 'Fisam'.

In comparison to the semi-double florets of 'Flocato', 'Fisdel' has double florets with a more round and closed shape. In addition, the plant habit of 'Fisdel' is more bushy, with shorter branches and internodes.

Although the main flower color of 'Fisdel' and 'Amethyst' is similar ,the florets of 'Fisdel' are smaller, nearly round and closed, with markings on its upper petals hardly visible. In contrast, 'Amethyst' has slightly zygomorph shaped florets, with distinct markings on its upper petals. The foliage of 'Fisdel' is darker green with distinct zonation and the leaves have a rounder shape with closed or overlapping base. By comparison, 'Amethyst' has wider leaves with open bases. Still further, plants of 'Amethyst' remain short, while those of 'Fisdel' are medium sized and start flowering considerably earlier.

The accompanying photographic drawing shows typical flower and foliage characteristics of 'Fisdel', with colors being as true as possible to illustrations of this type.

In the following description color references are made to The Royal Horticultural Society Colour Chart (R.H.S.). The color values were determined indoors from flowers taken from plants grown in a greenhouse in May 1995 in Hillscheid, Germany.

Classification:

*Botanical.*—A hybrid of the species *Pelargonium peltatum l'hert.*

*Commercial.*—Ivy geranium, cv. 'Fisdel'.

Inflorescence

Umbel:

*Shape.*—Semi-spherical.

*Average diameter.*—94 mm.

*Peduncle length.*—130 mm.

*Pedicel length.*—25 mm.

*Pedicel color.*—Light red.

*Number of flowers per umbel.*—11.

Corolla:

*Average diameter.*—48 mm.

*Form.*—Double.

*Shape.*—Round, closed.

*Number of petals.*—About 20.

*Number of petaloids.*—2–4.

*Color (general tonality from a distance of three meters).*—Violet.

*Color of upper petals.*—78 B.

*Markings on upper petals.*—Dark red veins and a small purple macule, frequently not visible since markings are usually covered by inner petals.

*Color of lower petals.*—78 B.

*Color of lower surface of petals.*—78 B-C.

*Color of sepals.*—Light to medium green.

*Number of sepals.*—7–8.

Bud:

*Shape.*—Elliptical.

*Color (adaxial).*—Medium green.

*Color (abaxial).*—Violet.

Reproductive organs:

*Androecium.*—0–2 fertile anthers, white filaments, yellow-orange pollen.

*Gynoecium.*—5–6-lobed stigma, purple-violet with white filament.

*Speed set.*—No spontaneous seed set observed.

Spring flowering response period: In Hillscheid, Germany, in 1995 plants had on average 0.4 flowers opened 15 weeks after planting of unrooted cuttings (pinched plants).

Outdoor flower production: The flower count in 1994 in Hillscheid, Germany indicated between 75 and 80 umbels per plant for May through August observation period.

Durability: Very good shatter resistance, average rain resistance.

Plant

Foliage:

*Form.*—Ivy shaped, with overlapping base.

*Margin.*—Entire.

*Size of leaf.*—7.6 cm.

*Color of upper surface.*—Medium to dark green, approximately 137 C.

*Color of zonation.*—Brown, about 166 A.

*Tolerance of botrytis.*—Good.

General appearance and form:

*Internode length.*—35 mm.

*Branching pattern.*—8.6 branches per plant after 16 weeks.

*Length of plants.*—70 cm, in mid September, based on 35-week-old plant.

CHART A

| | FISDEL | FISAM | AMETHYST |
|---|---|---|---|
| Flower color: | 78 B | 77 B | 78 B |
| Color of foliage: | Medium to dark green | medium green | light to medium green |
| Zonation | Weak–medium | Medium | Weak |
| Size of flowers | 47 mm | 54 mm | 55 mm |
| Diameter of leaf | 76 mm | 85 mm | 92.5 mm |
| Plant habit/length | 70 cm | 70 cm | 55 cm |
| Branching habit (number of branches) | 8.6 | 7.9 | 7.4 |

I claim:

1. A new and distinct cultivar of geranium plant named 'Fisdel', as illustrated and described.

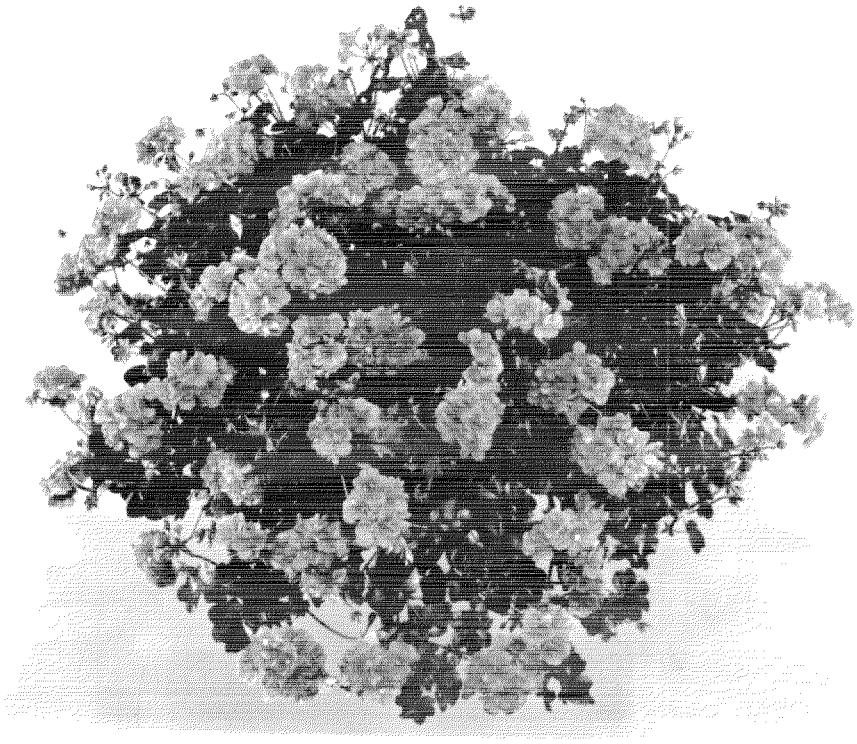

* * * * *